Figure 1:
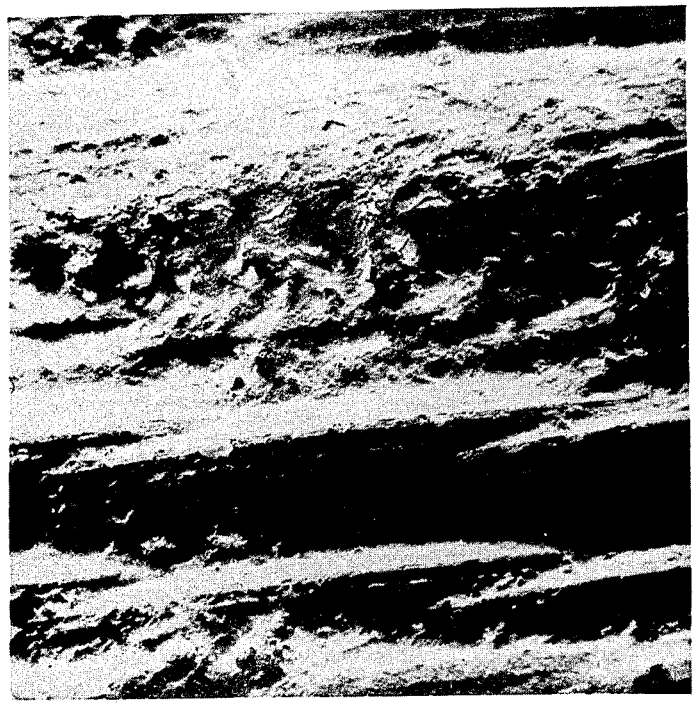

United States Patent [19]

Wåhlstam

[11] 4,363,795

[45] Dec. 14, 1982

[54] CLEANING AGENT FOR DENTINE SURFACES

[75] Inventor: Hans Wåhlstam, Vällingby, Sweden

[73] Assignee: Dental Therapeutics AB, Ektorp, Sweden

[21] Appl. No.: 229,581

[22] PCT Filed: Jun. 14, 1979

[86] PCT No.: PCT/SE79/00135

§ 371 Date: Feb. 15, 1980

§ 102(e) Date: Jan. 10, 1980

[87] PCT Pub. No.: WO80/00057

PCT Pub. Date: Jan. 24, 1980

[30] Foreign Application Priority Data

Jun. 15, 1978 [SE] Sweden .................................. 7806914

[51] Int. Cl.³ .............................................. A61K 7/22
[52] U.S. Cl. ........................................ 424/54; 424/49
[58] Field of Search .................................... 424/49, 54

[56] References Cited

U.S. PATENT DOCUMENTS 3,849,548 11/1974 Grand ..................................... 424/70
4,051,234 9/1977 Gieske et al. ........................... 424/52

FOREIGN PATENT DOCUMENTS 335068 2/1977 Austria .
1014289 8/1957 Fed. Rep. of Germany .
2415981 10/1975 Fed. Rep. of Germany .

*Primary Examiner*—Shep K. Rose
*Attorney, Agent, or Firm*—Cushman, Darby & Cushman

[57] ABSTRACT

Cleaning agent for dentine surfaces, particularly when mending teeth, the active constituents of which are invert soap (quaternary ammonium compounds), and ampholytic tenside and a complex forming agent being of aminocarboxylic acid type; the ampholytic tenside is preferably of dicarboxylated imidazoline type.

7 Claims, 2 Drawing Figures

CLEANING AGENT FOR DENTINE SURFACES

When teeth are mended, especially teeth attacked by caries, the tooth is usually bored (ground) and the attacked dentine is removed. An amorphous smear layer will then be produced adhering to the dentinal surface due to electrostatic attraction. The smear layer adhering to the dentine surface may contain microorganisms which can survive and grow below most types of fillings and their metabolism products may also damage the pulp. Thus, this amorphous smear layer should be removed and the dentinal surface be treated with an antibacterial cleaning solution as final step before filling or coating with a liner. It is essential that this is done so that the risk of bacterial growth in the space close to the dentinal surface is reduced as the retention of cement in the material insulating the dentine is improved. Such solutions should not have an irritating effect on the pulp when applied for about one minute. The known removal of the smear layer with demineralizing solutions is a questioned practice. While application of an acid on a dentinal surface for one minute has no irritating effect on the pulp, the orifices of the dentine channels expand and open and an even, organic film will remain between the channels. Therefore, the dentinal surface will be more difficult to dry and the adaptation to at least resinous materials is reduced. A dentinal surface with expanded dentine channels might result in an bacterial invasion in the dentine channels in case an infection should occur later.

Now, it has been found that the smear layer can be removed effectively from the dentinal surface by means of a cleaning agent which contains as active substituent an invert soap and an ampholytic tenside together with minor amounts of complex forming agents.

In the cleaning agent for dentinal surfaces according to the invention 10-90 parts by weight of an invert soap comprising a compound having the formula:

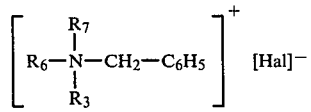

wherein $R_3$ and $R_7$ independent of each other or loweralkyl having 1-4 carbon atoms, both preferably being methyl, $R_6$ is alkyl having in average 8-16 carbon atoms and Hal is halogen, preferably chlorine, but also fluorine, bromine or iodine, are in combination with 90-10 parts by weight of an ampholytic (amphoteric tenside) comprising a compound having the formula

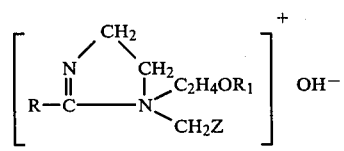

wherein R is the acyl radical of a fatty acid with 11-19 carbon atoms, $R_1$ is $CH_2.COOM$ or M, Z is $-COOM$, $-CH_2.COOM$ or

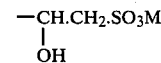

and M is an alkali metal, hydrogen or an organic base, or comprising a compound having the formula:

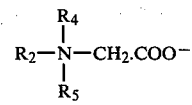

wherein $R_2$ is an alkyl group, preferably having 12-18 carbon atoms in average, or an alkylamino ethyl or alkylamino propyl radical having 8-18 carbon atoms or an acylaminoethyl or an acylaminopropyl radical, the acyl radical of which has in average 12-18 carbon atoms, and wherein $R_4$ and $R_5$ either both are methyl groups or wherein $R_4$ is hydrogen and $R_5$ is an electron pair. A complexing agent in minor amounts is always present. The complexing agent is a sequestering agent of aminocarboxylic acid type and the ratio between the amounts of invert soap and ampholytic tenside to complexing agent is preferably 100:1-1:100.

As is clear from the above the invert soaps are quaternary ammonium compounds. They have been used for a long time as disinfection agents; they are surface active and have a dirt dissolving ability.

The ampholytic tensides, e.g. of the type dicarboxylated imidazolines, have been used in shampooing agents, but also in deodorizing agents together with chlorohexidine. They have also been used as ampholytes in rust removers and metal cleaning agents.

The complex forming agents (the complexing agents, sequestering agents) are inter alia used analytically for forming complexes of metals, such as calcium.

The ampholytic (amphoteric) tenside can preferably be a tenside in the following groups of tensides:

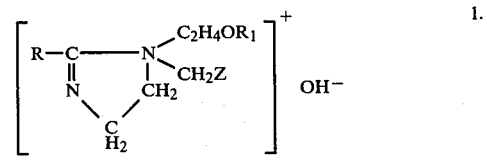

wherein R is the acyl radical of a fatty acid with, on an average, 11-19 carbon atoms, conveniently 13-17 carbon atoms, preferably 14-16 carbon atoms, $R_1$ is $CH_2.COOM$ or M, Z is $-COOM$, $-CH_2.COOM$ or

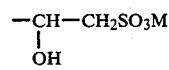

and M is an alkaline metal, H or the radical of an organic base, preferably an amine, which can be a heterocyclic amine or a triloweralkyl amine or a triloweralkanol amine, e.g. triethyl amine or triethanol amine.

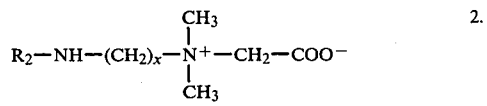

wherein R₂ is the acyl radical of a fatty acid with, on an average, 12–18 carbon atoms, and x is an integer of the value 1–4, preferably 2–3.

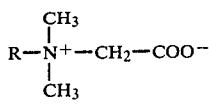

wherein R is an alkyl group, conveniently with 12–18 carbon atoms, preferably a mixture of 12–18 carbon atoms.

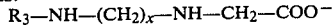

wherein R₃ is an alkyl group with, on an average, 8–18 carbon atoms, conveniently 10–14 carbon atoms, preferably 12 carbon atoms, and x is an integer of the value 1–4, preferably 2–3.

To sum up, these different groups of tensides 2–4 can be written as

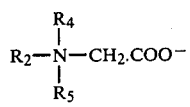

wherein R₂ is an alkyl group, conveniently with 12–18 carbon atoms, preferably a mixture of 12–18 carbon atoms or an alkylaminoethyl or alkylaminopropyl group with 8–18 carbon atoms, conveniently 10–14, preferably 12 carbon atoms (also a mixture with 8–18 carbon atoms is possible), or an acylaminoethyl or an acylaminopropyl group, where the acyl group has 12–18 carbon atoms on an average, preferably a mixture of 12–18 carbon atoms, and where R₄ and R₅ either both are methyl groups or where R₄ is H and R₂ an electron pair.

When M is an alkaline metal, it is preferably sodium, but can be lithium or potassium.

The proportion of the invert soap to the ampholytic tenside is not critical, but also extremely small amounts of the one constituent will produce a synergistic effect. Thus, 10–90 parts by weight of invert soap can be combined with 90–10 parts by weight of ampholytic tenside. However, the proportion is conveniently about 1:1, e.g. 30–70 parts by weight of invert soap and 70–30 parts by weight of ampholytic tenside, preferably 40–60 parts by weight of invert soap and 60–40 parts by weight of ampholytic tenside.

Normally the agent consists of an aqueous solution, in which the active constituents are usually included in an amount of at least 0.1 g, conveniently at least 1 g of these two substances together per 1 (liter) solution. There is no upper limit, but not more than 50 g is conveniently used, preferably not more than 10 g together of these substances per 1 solution. Moreover, the solution is conveniently buffered to the isoelectric point of the ampholytic tenside. This is usually in the neutral range, say about pH 6.5–7.5. It is also suitable to add fluorine compounds, such as sodium fluoride, potassium fluoride and sodium monofluorophosphate. The amount of fluorine containing compound can be up to 100 g per 1 solution, preferably maximum 50 g, say 20–35 g per 1 solution.

The complex forming agent (the sequestering agent) is e.g. of aminocarboxylic acid type, such as diethylene triamine pentaacetic acid, nitriloacetic acid; ethylene diaminotetraacetic acid is above all suitable. Salts of these acids can also be used, e.g. the sodium or potassium salts. These complex forming agents are preferably used in an amount of at least 0.1 g per 1 solution, e.g. 0.5–5 g, say 3 g. The upper limit of the used amount is not critical, but is dependent on the time during which the agent may act on the tooth. Amounts of up to 15 g per 1 solution have been tested with success, but the amount preferably used is 1–2 g per 1 solution.

It has been found that grinding debris which adheres well to a ground dentine surface by electrostatic attraction, is easily removed by this content of complex forming agent. This grinding debris has previously been removed by means of surface active agents, but at grinding with diamond grinding debris will adhere so strongly that even the surface active solutions will not provide quite satisfactory results.

It is known to remove grinding debris with ethylene diamine tetraacetic acid, but this treatment of the dentine surface has negative effects as it opens the orifices of the dentine channels and removes surrounding dentine, the surface becomes wetter and more difficult to drain and the treatment leaves a flat, thin film of organic substance, which may deteriorate the retention of cement and filling material.

As the present dentine cleaning agent contains complex forming agents, this can be used in such a concentration that no negative effects arise and the dentinal surface becomes satisfactorily cleaned also at diamond grinding. It has also been found that this complex forming agent has a synergistic effect as to the antibacterial properties of the present solution.

Conventional agents, such as other detergents, foaming agents, flavoring agents etc. can be added to the cleaning agent according to the invention.

The ingredients of the present cleaning agent for dentinal surfaces have been proposed and probably used alone, but not in combination, in agents for tooth and mouth care. They then act on the enamel surfaces of the teeth, but do not contact the dentine of the tooth. The Swedish patent No. 7113041-3 teaches ampholytic tensides, the German specification No. 1,014,289 and the Swedish specification No. 7508867-4 a complexing agent and the Austrian specification No. 335,068 invert soap in agents for tooth and mouth care.

A suitable invert soap for use according to the invention is alkyldimethylbenzyl ammonium chloride. Its LD₅₀ (lethal dose for 50% of the test animals) amounts to 1173 mg/kg body weight of rats. The tolerance of mucous membrane has been tested by applying once 0.1 ml to 10% and 5% diluted sample, respectively, to the conjunctival sack of a rabbit's eye. At these high concentrations irritation phenomena occurred in the form of red colouring.

The ampholytic tenside is ionically balanced and its isoelectric point is at a pH of about 7.0. The cationic and anionic groups have an equivalent strength and the ampholytic tenside is therefore miscible with all anionic, cationic and nonionic tensides in all proportions, even if it reacts more anionically in the alkaline range and more cationically in the acid range. Consequently, both the anionic and the cationic groups are weak in the present amphoteric tensides, the effect of which is that the compounds do not tend to form insoluble salts. The complete sodium salt is formed at pH 8–9 and the complete acid salts are formed at pH 5–6.

The present amphoteric tensides are non-toxic. The minimum lethal dose at intraperitoneal injection is, on an average, 4.0 g/kg. A simple lethal dose for 50% of the test animals is, on an average, 10–15 g/kg. Moreover, especially the coconut, lauric and capric acid derivatives have an evident detoxificating and reducing effect on other substances, e.g. alcohol, emulsifiers etc. Furthermore, these amphoteric tensides can be biologically broken down.

In the present antimicrobial agent the invert soap and the ampholyte show synergism.

Compounds within the group (2) are e.g. TEGO-betaine, L7, which is a fatty acid amidopropyl dimethylamino acetic acid betaine of the formula

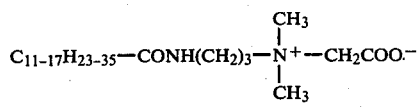

This compound contains consequently an acid amide group, a quaternary ammonium group and a carboxylic acid group.

Examples of compounds in the group (3) are compounds of the formulas

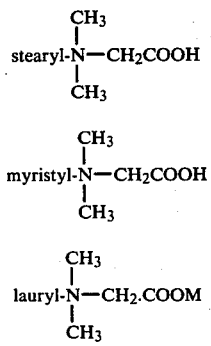

The hydrocarbon groups in these compounds are often mixtures of groups containing 12–14 or 10–18 carbon atoms.

An example of a compound in group (4) is TEGO 51, wherein $R_3$ is substantially a lauryl group (dodecyl); consequently the compound has the formula dodecyl—NH—CH$_2$CH$_2$—NH—CH$_2$COOH The invention is illustrated more closely by the following examples:

EXAMPLE 1

| | |
|---|---|
| Amphoteric-2[(1)] 38% | 0.30 g |
| Benzalkonium chloride | 0.10 g |
| EDTA-diNa—salt | 0.20 g |
| Buffer solution pH 7.3 | 1.00 g |
| Aqua dest. | ad 100 ml |

EXAMPLE 2

| | |
|---|---|
| Amphoteric-2[(1)] 38% | 0.30 g |
| Benzalkonium chloride | 0.10 g |
| EDTA-diNa—salt | 0.20 g |
| Sodium fluoride | 1.00 g |
| Buffer solution pH 7.3 | 1.00 g |
| Aqua dest. | ad 100 ml |

EXAMPLE 3

| | |
|---|---|
| Dodecyl-di-(aminoethyl)-glycine | 1.00 g |
| Benzalkonium chloride | 0.10 g |
| Nitrilotriacetic acid-diNa—salt | 0.20 g |
| Sodium fluoride | 3.00 g |
| Buffer solution pH 7.3 | 1.00 g |
| Aqua dest. | ad 100 ml |

EXAMPLE 4

| | |
|---|---|
| Fatty acid amidopropyl-dimethyl-amino-acetic acid betaine[(2)] | 0.80 g |
| Benzalkonium chloride | 0.20 g |
| DTPA-diNa—salt[(3)] | 0.20 g |
| Buffer solution pH 7.3 | 1.00 g |
| Aqua dest. | ad 100 ml |

[(1)]2-"cocoyl"-1-(sodium carboxymethyl)-1-2-(carboxymethoxy)ethyl-2-imidazolinium hydroxide

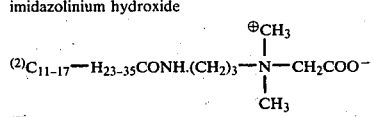

[(3)]Diethylene diamino pentaacetic acid-diNa—salt

For comparison, teeth to be extracted were ground with a diamond point using high speed, 200,000–300,000 r/min. The preparation was performed under water spray until flat areas of 1.5–2 mm$^2$ of the dentine were exposed. After preparation, the patients were allowed to rinse, thus contaminating the cut surfaces with saliva. Then, the surfaces were sprayed with ample amounts of water and dried for 5 seconds with compressed air before the experimental cleaning. The cleaning solution was applied by initial scrubbing of the surface for 5 seconds with a soaked cotton pellet. The solution was then allowed to remain in contact with the cut surface for 60 seconds before another 5 seconds of scrubbing. After final drying with an air jet for 5 seconds the tooth was extracted. The extracted tooth was immediately placed in a 10% neutral buffered formalin solution. Using conventional techniques, the ground surfaces were prepared and examined in a scanning electron microscope. The pictures were examined and graded by experienced examiners. The degree 0 represents dentine surface completely covered with a smear layer without anatomical details such as dentinal tubule apertures, while degree 3 represents a surface with the tubul apertures open and slightly filled with cutting debris and with the intertubular areas without any signs of smear layer.

Figure 2:
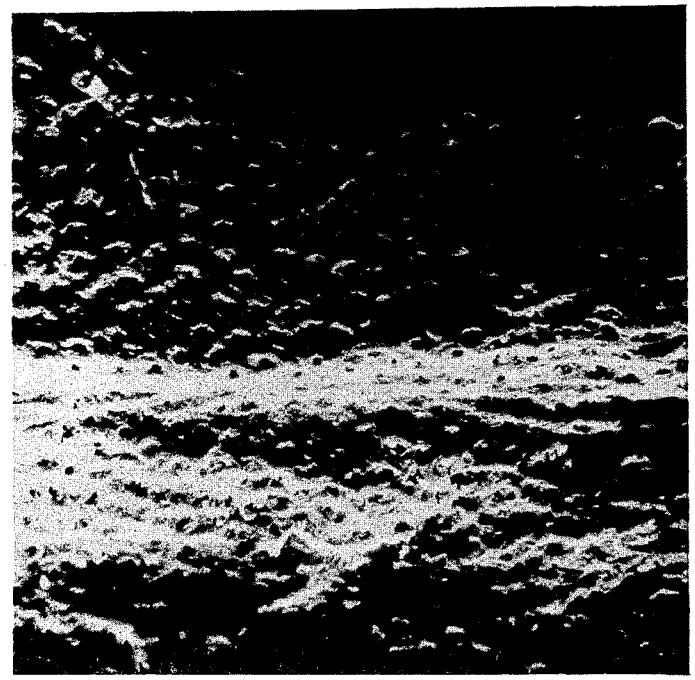

For this comparison, the known solution (Tubulicid Blue Label ®) and a solution according to example 1 were used. The results are shown on the accompanied drawing where FIG. 1 shows the result obtained by the known solution and FIG. 2 shows the result obtained by the solution of example 1. The known solution contains chlorohexidine-digluconate 0.1 g; dodecyldiamino ethyl glycine (9% solution) 1.0 g; aqua dest. ad 100 g.

The cleanliness of FIG. 1 is estimated to grade 1; a thin amorphous smear layer covers the surface. Deposition of tubule apertures is indicated by slight elevations. The magnification is 1100×.

The surface shown in FIG. 2 is graded 3; the tubule apertures are clearly visible; magnification 1100×.

Thus, a cleaning solution according to the present invention has the ability to remove most of smear layer produced during grinding without opening too many tubule apertures or removing peritubular dentine.

The cleaning agent of example 1 being the preferred solution, thus, behaves in an unexpected way by removing most of the smear layer without causing damage to the dentinal surface itself.

What is claimed is:

1. A cleaning agent for dentine surfaces, comprising 10 to 90 parts by weight of (1) benzalkonium chloride, and
90 to 10 parts by weight of (2) an ampholytic tenside having the formula

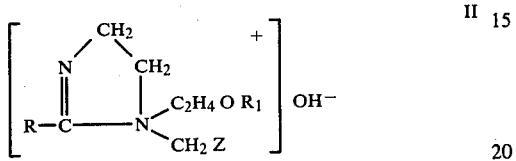

wherein R is the radical of a fatty acid having on an average of 11 to 19 carbon atoms, $R_1$ is $-CH_2.COOM$ or M, Z is $-COOM$ or $-CH_2.COOM$ and M is an alkali metal or hydrogen, together with (3) an aminocarboxylic acid sequestering agent, wherein the ratio between the amount of benzalkonium chloride and ampholytic tenside to sequestering agent is from 100:1 to 1:100.

2. The cleaning agent according to claim 1 wherein M is sodium.

3. The cleaning agent according to claim 1 or 2 wherein the sequestering agent is ethylenediamine tetraacetic acid or a salt thereof.

4. The cleaning agent according to claim 1 wherein the sequestering agent is ethylenediamine tetraacetic acid or a salt thereof and is in an aqueous solution in which the benzalkonium chloride and the ampholytic tenside are present in an amount of 0.1-10 g per liter of solution and the sequestering agent is present in an amount of 0.1-10 g per liter solution.

5. The cleaning agent according to claim 4 in an aqueous solution wherein the ampholytic tenside and the benzalkonium chloride together are present in an amount of from 0.1 to 10 grams per liter and the EDTA sequestering agent is present in an amount of from 0.1 to 10 grams per liter of solution.

6. The cleaning agent according to claim 5 wherein the ampholytic tenside is 2-"cocyl"-1-(sodium carboxymethyl)-1-2-(carboxymethoxy)ethyl-2-imidazolinium hydroxide.

7. A cleaning agent for dentine surfaces, comprising 10 to 90 parts by weight of (1) benzalkonium chloride, and
90 to 10 parts by weight of (1) an ampholytic tenside comprising a compound having the formula:

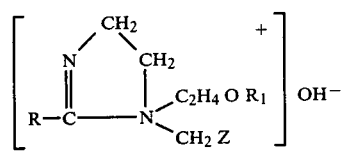

wherein R is the radical of a fatty acid having on an average of 11-19 carbon atoms, $R_1$ is $-CH_2.COOM$ or M, Z is $-COOM$, $-CH_2.COOM$ or

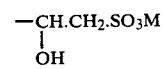

and M is an alkali metal, hydrogen or the residue of an organic base, or comprising a compound having the formula:

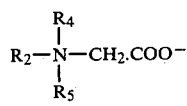

wherein $R_2$ is an alkylamino ethyl or propyl group, the alkyl group having 8 to 18 carbon atoms, or an acylamino ethyl or acylamino propyl group, the acyl group of which has 12 to 18 carbon atoms on an average and wherein $R_4$ and $R_5$ both are methyl groups or $R_4$ is hydrogen and $R_5$ is an electron pair, and (3) an aminocarboxylic acid sequestering agent wherein the ratio between the amount of benzalkonium chloride and ampholytic tenside to sequestering agent is 100:1 to 100:1.

* * * * *